(12) United States Patent
Rusa

(10) Patent No.: US 11,883,060 B2
(45) Date of Patent: Jan. 30, 2024

(54) VERSATILE FOLLICULAR TRANSPLANT METHOD AND SYSTEM

(71) Applicant: Advanced Hair Restoration LLC, Bellevue, WA (US)

(72) Inventor: Nik Rusa, Bellevue, WA (US)

(73) Assignee: Advanced Hair Restoration LLC, Bellevue, WA (US)

( * ) Notice: Subject to any disclaimer, the term of this patent is extended or adjusted under 35 U.S.C. 154(b) by 225 days.

(21) Appl. No.: 15/701,359

(22) Filed: Sep. 11, 2017

(65) Prior Publication Data

US 2019/0076163 A1    Mar. 14, 2019

(51) Int. Cl.
| | |
|---|---|
| *A61B 17/3205* | (2006.01) |
| *A61B 17/34* | (2006.01) |
| *A61B 17/00* | (2006.01) |
| *A61F 2/10* | (2006.01) |
| *A61B 17/30* | (2006.01) |

(52) U.S. Cl.
CPC .... *A61B 17/32053* (2013.01); *A61B 17/3468* (2013.01); *A61B 2017/00752* (2013.01); *A61B 2017/306* (2013.01); *A61F 2/10* (2013.01)

(58) Field of Classification Search
CPC .......... A61B 17/32053; A61B 17/3468; A61B 2017/00752; A61B 2017/320064; A61F 2/10

See application file for complete search history.

(56) References Cited

U.S. PATENT DOCUMENTS

| | | | |
|---|---|---|---|
| 5,782,851 A | 7/1998 | Rassman | |
| 2006/0161179 A1* | 7/2006 | Kachenmeister | ........................... A61B 17/32053 606/133 |
| 2016/0166272 A1* | 6/2016 | Shiao | ............... A61B 17/32053 606/133 |
| 2019/0282260 A1* | 9/2019 | Erdogan | .......... A61B 17/32053 |

FOREIGN PATENT DOCUMENTS

WO    WO-2017196157 A1 * 11/2017 ......... A61B 10/0233

* cited by examiner

*Primary Examiner* — Sarah A Long
(74) *Attorney, Agent, or Firm* — John J. Bamert, Esq.; Bamert Regan PLLC

(57) ABSTRACT

Provided are methods and systems for transplanting follicles and other cells from one location on a patient to another location on the same or different patient without the need to shave or cut hair extending from the follicles or cells.

21 Claims, 3 Drawing Sheets

VERSATILE FOLLICULAR TRANSPLANT METHOD AND SYSTEM

FIELD

Provided are methods and systems for transplanting follicles and other cells from one location on a patient to another location on the same or different patient without the need to shave or cut hair extending from the follicles or cells.

BACKGROUND

Follicular units are clusters of hairs which emerge from a single site on the scalp. Usually a unit contains between a single hair to as many as four hairs each. Follicular units also include ancillary structures to the hair cells, including sebaceous glands, nerves, musculature and a protective dermis. At present, two main methods for surgical hair transplantation are practiced to provide restoration of facial and cranial hair through transplantation of follicular units.

The first, follicular unit transplantation (FUT), is a surgical technique where a strip of follicle containing skin and hair follicles is excised and later dissected under a microscope to extract individual follicular units, as described in U.S. Pat. No. 5,782,851. The purpose of FUT is to preserve individual units intact during transplantation, to improve the viability of transplanted hair. The surgical removal of the strip of skin takes place in a "safe donor region," that is expected to contain hair that is healthy and suitable for transplantation. The surgery invariably leaves a linear scar that remains hidden while the hair is worn long. However, if the patient chooses to wear his or her hair short or experiences further thinning of the hair, the scar can become conspicuously visible.

The second transplantation method is follicular unit extraction (FUE). In a FUE process, the donor area is shaved/trimmed down to approximately 1 mm in length. This allows a FUE device and/or user to be positioned over the graft without interference from the hair. Then, the device is used to simply cut the tissue around the graft and remove the graft. FUE involves a shorter recovery time and significantly lower post-operative discomfort that FUT, but the requirement to cut or shave the hair can be disruptive to patient productivity, comfort and lifestyle. Many potential patients report avoiding or postponing the procedure due to the requirement of cutting or shaving their hair.

A third surgical method, as yet unavailable to the public, is a subdermal endoscopic method developed under the trade name, Pilofocus, that is designed to entirely eliminate the formation of scar tissue from the donor region. While promising to result in fewer visible signs of transplantation, the technology involves endoscopic surgery.

Therefore, in the absence of an invasive surgical procedure, the transplantation of follicles from one tissue to another requires shaving of the hair emanating from the follicle. This can be burdensome or even unacceptable to many patients for varying reasons. For example, some patients wish to conceal the fact that a procedure has been done from the public. Others may have professions or other duties which prevent them from significantly altering their appearance (by means of a very close haircut, for example).

SUMMARY

Some embodiments of the present disclosure relate to a method of extracting a single follicular unit (a "follicle") comprising hair or hairs ("the hair") over about 1 mm in length from the skin of a subject comprising placing the hair coming out of the follicle against the skin adjacent to the follicle, placing the bladed end of a cutting tool device above the follicle, pinching the hair between the skin and the cutting tool device, cutting the hair with the cutting tool device, cutting the skin around the follicle with the cutting tool device, extracting the follicle from the skin of the subject, and leaving surrounding hair uncut.

In some embodiments, the hair emerging from the follicle is cut to a length of about 1 mm.

In some embodiments, the hair is cut prior to the removal of the follicle from the skin of the subject.

In some embodiments, the cutting tool device further comprises a rotating cutter head element.

In some embodiments, the hair comprises angling the cutting tool device to pinch the hair between the cutting tool device and the skin In some embodiments, the hair is over about 3 mm in length.

In some embodiments, the hair is over about 10 mm in length.

In some embodiments, cutting the hair comprises rotating the cutter head element of the cutting tool device.

Some embodiments further relate to separating the hair on the skin of the subject into strips which are separated by a separator material.

In some embodiments, the separator material is gauze.

In some embodiments, the cutting tool device comprises tubing.

In some embodiments, the tubing is configured to transport saline and provide suction to remove the follicle from the skin of the subject.

In some embodiments, removing the follicle from the skin of the subject comprises exerting suction on the follicle to move it from the skin of the subject into saline within the tubing.

Some embodiments further relate to moving the follicle through the tubing into a receptacle.

Some embodiments relate to an apparatus for removing a follicle comprising hair over about 1 mm in length from the skin of a subject comprising a cutting tool device comprising a cutter head element and tubing configured to transport saline and provide suction, a vacuum pump, and a receptacle.

In some embodiments, the cutter head element is configured to rotate.

In some embodiments, the cutter head element is cylindrical and hollow.

In some embodiments, the tubing is connected to the cutter head element, the vacuum pump and the receptacle.

Some embodiments further relate to a three-way connector connected through the tubing to the cutter head element, the vacuum pump and the receptacle.

In some embodiments, the receptacle is configured to collect the extracted follicular units.

In some embodiments, the receptacle is configured to contain saline solution.

DETAILED DESCRIPTION

Figure 1:
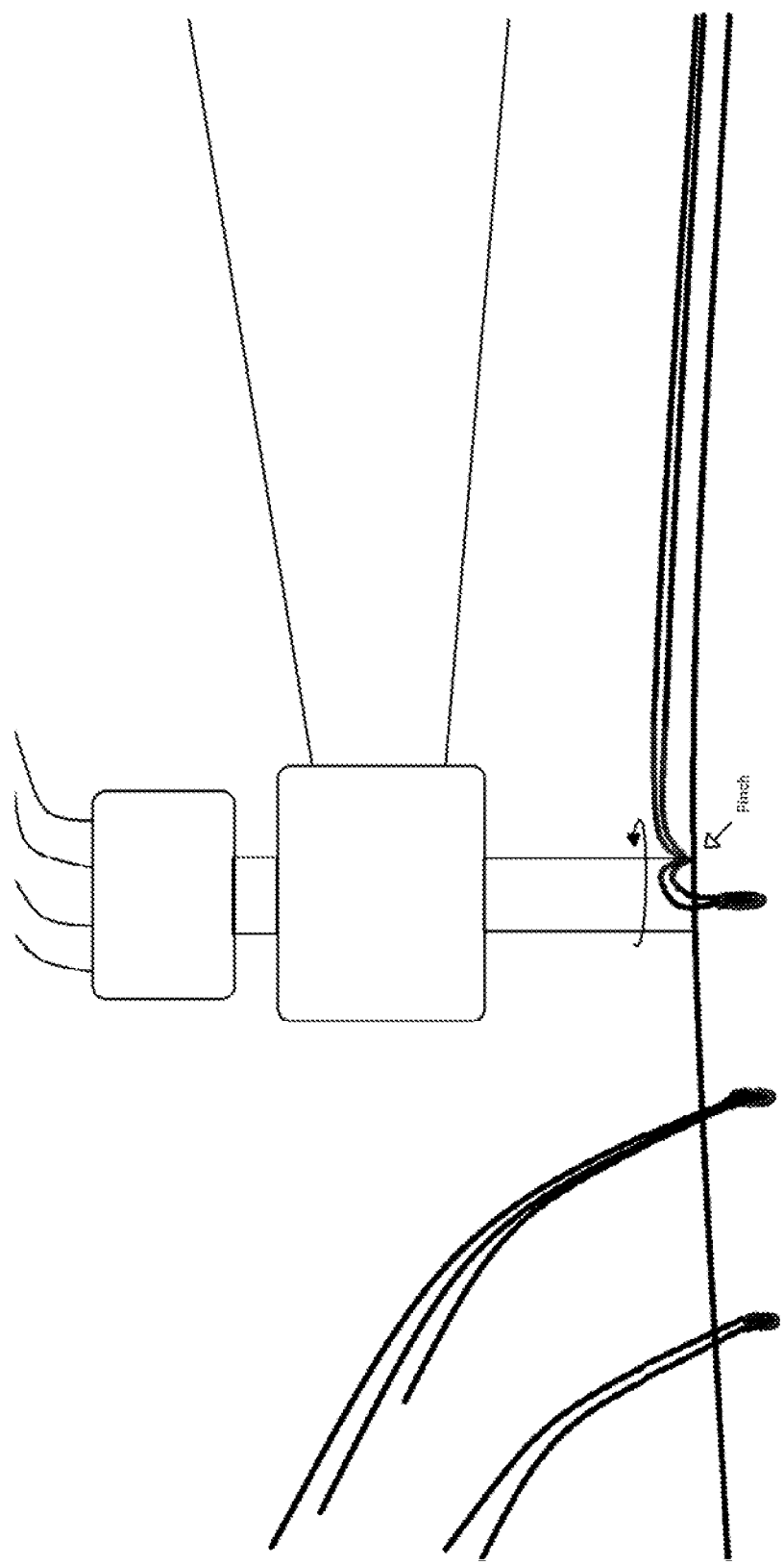
FIG. 1 is a diagram illustrating an overview of one embodiment of the present disclosure in which a punch device is positioned over a portion of a patient's scalp corresponding to a follicle to be extracted and pinching the hair extending from the follicle between the punch device and the scalp.
Figure 2:
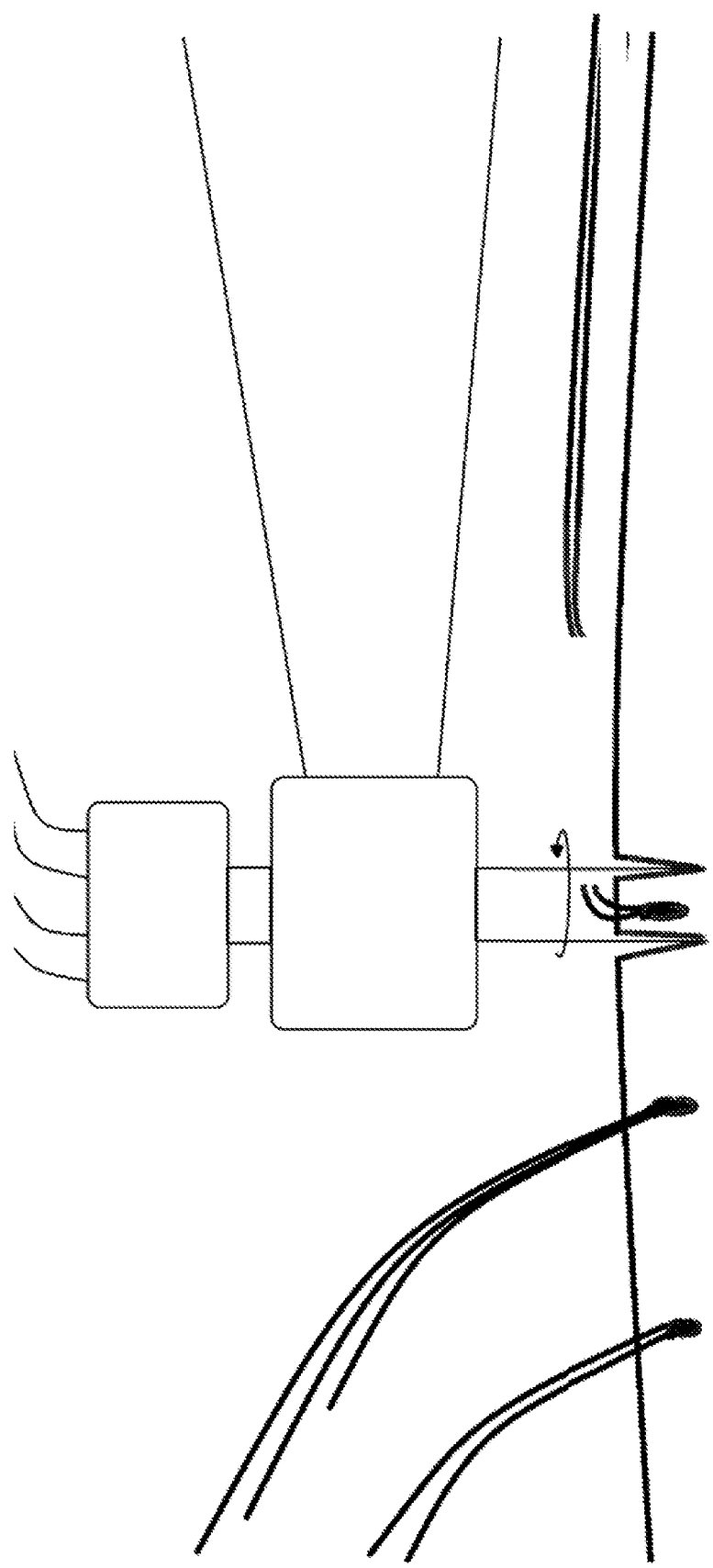
FIG. 2 is a diagram illustrating an overview of one embodiment of the present disclosure in which the punch device has cut the hair extending from the follicle and is used to cut the patient's scalp around the follicle.
Figure 3:
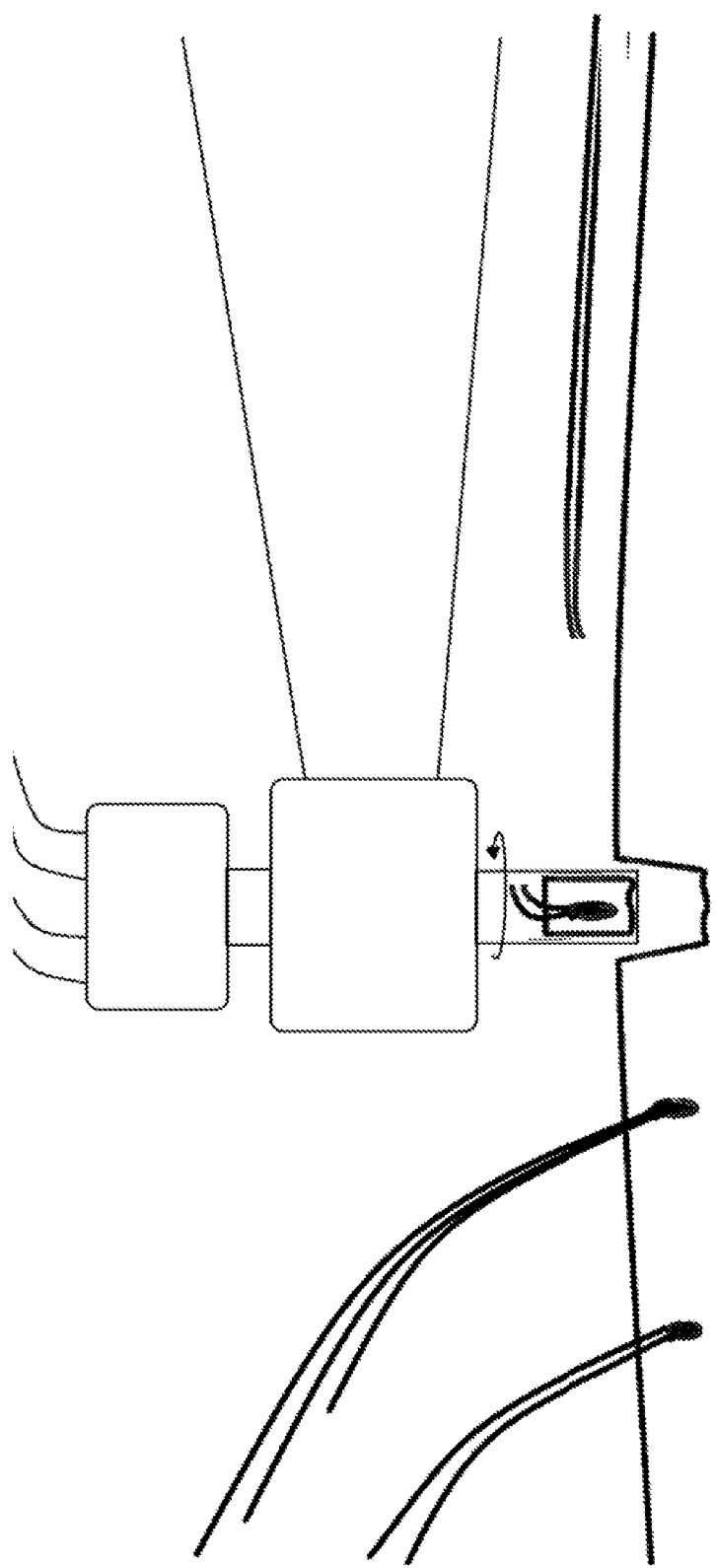
FIG. 3 is a diagram illustrating an overview of one embodiment of the present disclosure in which the follicle has been removed by the punch device from the surrounding scalp tissue.

The following discussion is presented to enable a person skilled in the art to make and use one or more of the present embodiments. The general principles described herein may be applied to embodiments and applications other than those detailed below without departing from the spirit and scope of the disclosure. Therefore, the present embodiments are not intended to be limited to the particular embodiments shown, but are to be accorded the widest scope consistent with the principles and features disclosed or suggested herein.

Generally, the nomenclature and terms used herein are those well-known and commonly employed in the art. Unless defined otherwise, all technical and scientific terms used herein generally have the same meaning as commonly understood by one of ordinary skill in the art to which this disclosure belongs.

The term "subject" or "patient" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

Language of degree used herein, such as the terms "approximately," "about," "generally," and "substantially" as used herein represent a value, amount or characteristic close to the stated value, amount or characteristic that still performs a desired function or achieves a desired result. For example, the terms "approximately," "about," "generally," and "substantially" may refer to a value, amount, or characteristic that is within less than 10% of, within less than 5% of, within less than 1% of, within less than 0.1% of, and within less than 0.01% of the stated value, amount, or characteristic. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. The term "about," when used before a number, discloses both the exact number and numbers that are approximately equal to the number." The term "drug" refers to a compound, or a pharmaceutical composition thereof, which is administered to a subject for treating, preventing or ameliorating one or more symptoms of a condition, disorder or disease.

Many challenges are associated with performing hair transplant processes (such as FUE processes) without shaving or cutting the patient's hair close to the head. Dealing with blood that accumulates and clots in the longer hair presents several clinical issues. During the traditional shaved process the blood can easily be wiped from the skin with a gauze pad. However, with long hair, wiping the hair does not allow gauze or other wipes to pick up all the blood trapped between the layers of hair. The hair that is clotted with the dried blood becomes hard and difficult to harvest. In addition, the surrounding long hair can get in the way of the working area leading to decreased efficiency and increased costs.

In addition, FUE processes often rely on the clinician manually removing a graft with tweezers after it has been cutout/scored. With longer hair, such grafts can be easily lost or difficult to find amongst other long hairs. The increased difficulty and amount of time involved in attempting a process without shaving or cutting the hair close to the head makes the process untenable, especially when a moderate to large number of follicles are to be transplanted.

Some embodiments of the present disclosure relate to a system and method allowing longer hair to be harvested and transplanted efficiently without shaving the surrounding area. In some embodiments, the clinician can lightly pull the hair down to the skin in order to allow clear visibility of the base of the hair graft on the scalp, then position a "punch" device capable of cutting the surrounding tissue over the hair graft area. Then, the clinician uses the punch device to pinch the hair shaft between the punch and the scalp. The punch device is then activated so that it spins. The clinician applies pressure to the hair and underlying skin and both cuts the hair down to the appropriate length (e.g. from about 1 mm to about 5 mm above the scalp) and cuts the skin surrounding the graft allowing the graft to be suctioned into the punch. In some embodiments, the graft then travels from the punch device into tubing or other means of conveyance, and ultimately into a collection receptacle, such as a jar.

In some embodiments, the method can be used to address accumulating blood from the donor area. The clinician separates thin strips of hair as a working area at one time. The layers of hair that are below/outside of the current working area can be lifted up with gauze or other material placed underneath. Then an instrument such as a comb is placed into the lifted layer of hair. Regularly, the clinician will run the comb through the lifted layer of hair to remove blood, prevent clotting and separate tangled hairs. Other related longer hair not subject to blood clotting, can be pulled away and held in place with a rubber band, tape, or other product.

Some embodiments include a suction and saline system that is utilized to automatically suck up the graft to be collected and stored. This way, the clinician is not required to then remember/find the grafts that have been cut out and collect them. This significantly reduces the time and difficulty of the process. The saline hydration used in the method significantly increases the level of viability of the graphs throughout the process, both increasing yield and enhancing the results of the process.

EXAMPLES

In one example, the system and method described above can be applied to a patient without previously shaving the donor region. Therefore, the patient has the option of getting a short styled haircut or leaving their hair long prior to the process, depending on their preference.

In another example, the system and method described above can be used directly on a patient's hair, without using micro-tweezers to capture the extracted follicle. This greatly improves the efficiency of the process and enhances the viability of the harvested grafts. Reducing the amount of time a patient is required to be present for the procedure is beneficial both to the patient and the practitioner.

In another example, the system and method described above can be applied to a patient having hair of a length approximately 1 mm or more, and personal or professional reasons to maintain it at that length. In such a case, no existing hair transplantation technique, neither FUE nor FUT would be able to provide the desired results.

In another example, the system and method described above can be applied to a patient having hair of a length approximately 5 mm or more. Again, the uniqueness of the present embodiment allows for the procedure to be performed on hair of many different lengths.

In another example, the system and method described above can be applied to a patient having hair of a length approximately 10 mm or more.

In another example, the system and method described above can be applied to a patient having hair of a length approximately 100 mm or more.

In another example, the system and method described above can be used to minimize the appearance of FUE treatments by only cutting the hairs from follicular units that are to be extracted, leaving neighboring hairs from the safe donor region unaffected and minimizing the visual impact of the surgery on the patient's hair. Many patients wish to conceal the fact that a procedure was performed and prefer methods which reduce the appearance of such a procedure.

In another example, a patient with a smaller than normal number of eligible follicular units, or with thinner than average hair in the safe donor regions, can use the system and method described above to leave the remaining hair at its initial length. This can be very important to patients who prefer to alter the look of their hair as little as possible as a result of the procedure.

In another example, the system and method described above can be used to minimize the appearance of FUE treatments by reducing the number of follicular units that are needed, by taking advantage of the suction and saline system. By enhancing the viability of the follicles collected, fewer follicles will be needed to achieve the desired result. This way, a patient may ultimately achieve far superior results with multiple procedures compared to what was previously available.

In another example, the system and method described above can be used to help a surgeon keep track of extracted follicular units by leaving intact hair at its natural length, while cutting extracted hair to a length of about 1 mm-about 5 mm. In this way, extracted follicular units that are not otherwise removed by the suction and saline system will be identifiable as lone short hair segments.

In another example, the system and method described above can be used to collect fewer hairs in a given surgical procedure, by storing extracted follicles in saline solution pending implantation, as a means to increase the efficiency of extraction.

In another example, the system and method described above can be used when blood released by the skin upon extraction of the hair is coating hairs in the area of the follicle to maintain visibility and reduce the number of lost follicles.

The examples set forth above are provided to provide those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents and patent applications cited in this specification are incorporated herein by reference in their entireties as if each such publication, patent or patent application were specifically and individually indicated to be incorporated herein by reference.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure and protected by the following claims.

I claim:

1. A method of extracting a single follicle of a patient, the follicle having hair that extends over about 1 mm in length away from skin of the patient, the method comprising:
    placing the hair against a portion of the skin that is adjacent to the follicle;
    pinching the hair between the portion of the skin and a cutting tool device;
    cutting the pinched hair with the cutting tool device;
    cutting the skin around the follicle with the cutting tool device; and
    extracting the follicle from the skin of the patient,
    whereby cutting the pinched hair with the cutting tool device facilitates extracting the follicle from the skin of the patient while hairs of the patient surrounding the pinched hair remain extending over 1 mm in length away from the skin of the patient.

2. The method of claim 1, wherein cutting the pinched hair with the cutting tool device includes cutting the hair to a length of about 1 mm.

3. The method of claim 1, wherein cutting the pinched hair with the cutting tool device includes cutting the hair prior to extracting the follicle from the skin of the patient.

4. The method of claim I, wherein the ting tool device includes a rotating cutter head.

5. The method of claim I, wherein pinching the hair includes angling the cutting tool device to pinch the hair between the cutting tool device and the skin.

6. The method of claim 1, wherein pinching the hair includes pinching the hair while the hair is over about 3 mm in length.

7. The method of claim 1, wherein pinching the hair includes pinching the hair while the hair is over about 10 mm in length.

8. The method of claim 1, wherein cutting the pinched hair comprises rotating a cutter head of the cutting tool device.

9. The method of claim 1, further comprising separating hairs of the patient into strips that are separated by a separator material.

10. The method of claim 9, wherein the separator material is gauze.

11. The method of claim 1, wherein the cutting tool device has tubing.

12. The method of claim 11, wherein the tubing is configured to transport saline and to provide suction to remove the follicle from the skin of the patient.

13. The method of claim 11, wherein extracting the follicle from the skin of the patient includes suctioning the follicle from the skin of the patient.

14. The method of claim 13, further comprising moving the extracted follicle through the tubing into a receptacle containing saline.

15. The method of claim 1, wherein the cutting tool device includes a cutter head configured to surround the follicle while the follicle is in the skin of the patient, wherein tubing is fluidly coupled to the cutter head, wherein a vacuum pump is fluidly coupled to the tubing and is configured to create suction in the tubing, wherein a receptacle is configured to receive the follicle from the tubing after the cutter head of the cutting tool device cuts the skin around the follicle and after the follicle is suctioned away through the tubing and away from the skin of the patient.

16. The method of claim 15, wherein the cutter head is configured to rotate.

17. The method of claim 15, wherein the cutter head is cylindrical and hollow.

18. The method of claim 15. wherein the tubing is to the cutter head, the vacuum pump, and the receptacle.

19. The method of claim 15, wherein a three-way connector is connected through the tubing to the cutter head element, the vacuum pump and the receptacle.

20. The method of claim 15, wherein the receptacle is configured to collect the extracted follicle.

21. The method of claim 15, wherein the receptacle is configured to store the extracted follicle in a saline solution.

* * * * *

UNITED STATES PATENT AND TRADEMARK OFFICE
CERTIFICATE OF CORRECTION

PATENT NO. : 11,883,060 B2
APPLICATION NO. : 15/701359
DATED : January 30, 2024
INVENTOR(S) : Nik Rusa Page 1 of 1

It is certified that error appears in the above-identified patent and that said Letters Patent is hereby corrected as shown below:

In the Specification

In Column 1, Line 42, delete "that" and insert -- than --, therefor.

In Column 2, Line 18, delete "skin" and insert -- skin. --, therefor.

In Column 3, Line 63, delete "number."" and insert -- number. --, therefor.

In Column 4, Line 6, delete "shaved" and insert -- shaving --, therefor.

In the Claims

In Column 6, Line 54, in Claim 4, delete "claim I, wherein the ting tool device" and insert -- claim 1, wherein the cutting tool device --, therefor.

In Column 6, Line 56, in Claim 5, delete "claim I," and insert -- claim 1, --, therefor.

In Column 8, Lines 14–15, in Claim 19, delete "to the cutter head element, the vacuum pump and the receptacle." and insert -- to the cutter head element, the vacuum pump, and the receptacle. --, therefor.

Signed and Sealed this
Twenty-first Day of October, 2025

John A. Squires
*Director of the United States Patent and Trademark Office*